_United States Patent_ [19]

Iizuka

[11] 4,307,193

[45] Dec. 22, 1981

[54] METHOD OF PRODUCING INTERFERON

[75] Inventor: Masahiko Iizuka, Fujisawa, Japan

[73] Assignee: Toray Industries, Inc., Tokyo, Japan

[21] Appl. No.: 95,955

[22] Filed: Nov. 20, 1979

Related U.S. Application Data

[60] Continuation of Ser. No. 914,049, Jun. 9, 1978, abandoned, which is a division of Ser. No. 742,250, Nov. 16, 1976, abandoned.

[51] Int. Cl.$^3$ .............................................. C12P 21/00
[52] U.S. Cl. ...................................... 435/68; 435/811
[58] Field of Search ........................... 435/68, 285, 811

[56] References Cited

U.S. PATENT DOCUMENTS

| | | | |
|---|---|---|---|
| 3,773,924 | 11/1973 | Ho | 435/68 |
| 3,843,454 | 10/1974 | Weiss | 435/285 |
| 3,951,740 | 4/1976 | Gresser et al. | 435/68 |
| 4,007,086 | 2/1977 | Hamilton | 435/68 |

_Primary Examiner_—Alvin E. Tanenholtz
_Attorney, Agent, or Firm_—Austin R. Miller

[57] ABSTRACT

In the method of the present invention for production of interferon from propagating tissue culture cells, a propagating apparatus is utilized having a plurality of spaced-apart parallel flat plates. Monolayers of the tissue cells are grown on these plates and the apparatus is adapted for the introduction of gas and/or liquid mediums between the plates. In carrying out the method of the present invention the culture medium which nourishes the propagating cell tissues is exposed to a gas phase for oxygenating and adjusting the pH of the medium, while maintaining the culture medium and the propagated cells in a static and undisturbed condition.

5 Claims, 11 Drawing Figures

METHOD OF PRODUCING INTERFERON

This is a continuation of application Ser. No. 914,049, filed 6/9/78, and now abandoned which in turn is a divisional application of Ser. No. 742,250, filed Nov. 16, 1978 now abandoned.

INTRODUCTION

Recently, it has been recommended that live viral vaccines for human use (poliomyelitis, rubella or measles) be produced by normal human diploid cell strains in cultures. To accomplish this purpose, development of a suitable technique and apparatus for cultivating these cells is needed and desired.

Heretofore, essentially two methods have been available for cell cultivation: one, a monolayer culture technique and the other, a suspension culture technique to which human diploid cells are not yet adaptable. At present, these cells grow only under monolayer culture conditions.

Conventional monolayer cultivation is performed with glass or plastic bottles or with Petri dishes. Sterilized culture media containing a suspension of cells is placed into the bottles or dishes, the cells adhere to the bottom surfaces of the vessels, grow, and finally form sheets on the surfaces. The space above the culture media is, of course, filled with air.

Cell cultivation by the above method requires cell growth on the surfaces of a great many small vessels in order to obtain sufficient amounts for production of biological products. Since cell cultures require aseptic handling, treatment of a large number of small vessels is both cumbersome and timeconsuming. Also, the volume occupied by large numbers of these vesels is wasteful of space.

Other apparatus and methods recently devised to eliminate the above disadvantages, such as the roller bottle cultivation; multi-disc tissue propagators; multiplate, and sterilic-type apparatus, while providing a large surface area in a small, totally-occupied volume which can be handled easily, require movement between the cell sheets and the culture media, unlike the static monolayer culture technique, in order to provide sufficient oxygen supply to the cells due to the larger surface area. One means of supplying oxygen utilized by these techniques is to circulate the oxygenated media, and the other means is the reciprocating movement of a cell sheet across the air phase and the liquid phase.

Movement of the cell sheet and/or the culture medium causes difficulty in the maintenance of the microenvironment of the cells, and microexudate, for example carpet protein which is secreted from the cells may diffuse, thus inhibiting cell growth. Cells of low density are particularly affected by loss of the microexudate.

SUMMARY OF THE INVENTION

The present invention relates to a method and apparatus for growing animal cells, and in particular, to a method and apparatus for growing cell cultures on a large scale. Such large scale growth systems are desirable in view of the large quantities of cells required in the development and production of biological products such as viral vaccines, interferon, enzymes such as urokinase, and hormones.

Therefore, it is a principal object of the present invention to provide a large surface area for cell growth in a small total volume wherein a sufficient oxygen supply is provided without movement of the cells and culture media and thus eliminating any diffusion of microexudate.

This and other objects of the present invention will become more readily apparent from the following description of the drawings, taken in conjunction with the appended specification.

DRAWINGS

DETAILED DESCRIPTION OF THE INVENTION

Figure 1:
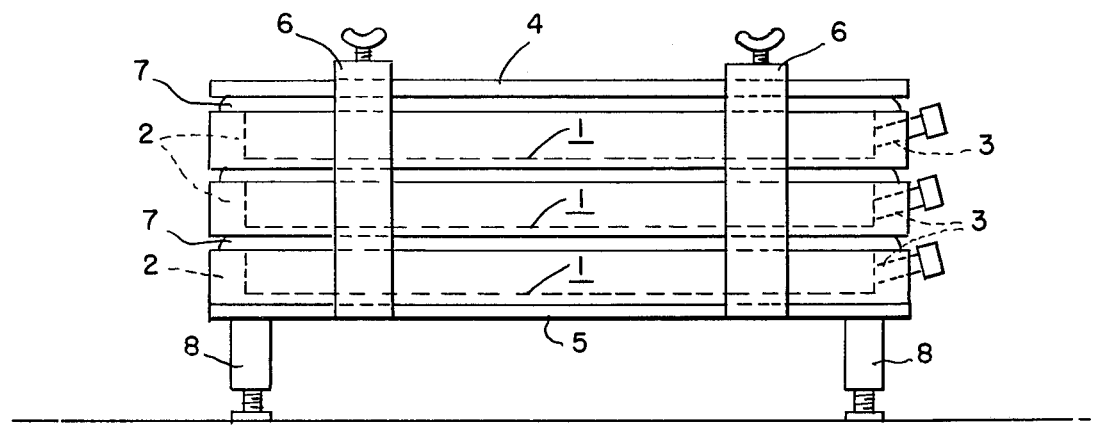
FIG. 1 is a side view of one form of the apparatus of the present invention, showing a stacked-dish culture apparatus with the medium and gas being independent of one another.

Functionally, the present invention is similar to the bottle system wherein stacks of gas phase, liquid phase and cell layers are repeated in one apparatus. To employ this system, applicants have shown in the drawings two types of apparatus, both of which comprise a plurality of flat, spacedapart plates for cell attachment on which the gas, liquid and cells can exist in parallel position.

Figure 2:
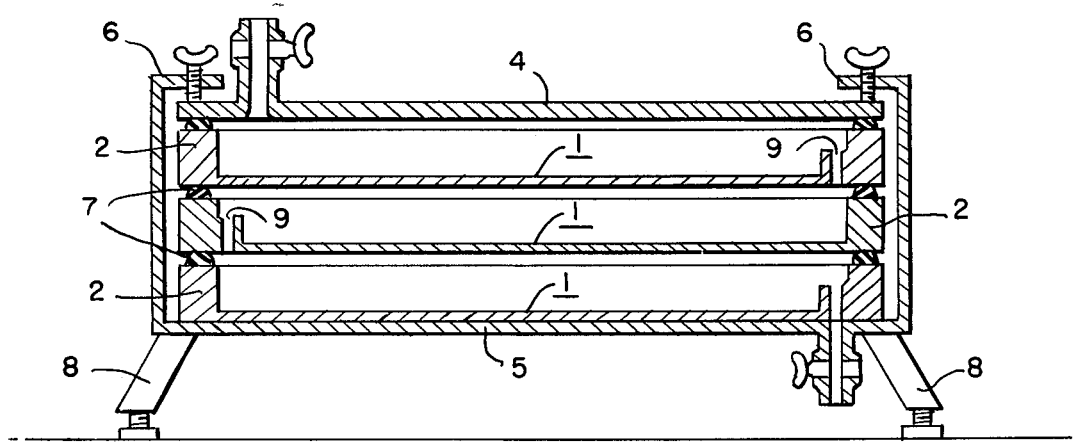
FIG. 2 is a view, in cross-section, of the apparatus of FIG. 1, in which the dishes have overflow passages through which liquids or gases can pass.

Referring now to the drawings, and with particular reference to FIG. 1, culture dishes are provided comprising cell attachment plates 1 on which confluent monolayers of cells are grown, and frames 2 enclosing the plates. Inlet/outlet ports 3 are provided on the sides of the culture dishes for passage of the medium and of the phase which is used for oxygenating and adjusting the pH of the medium gas. These inlet/outlet ports 3 can be stoppered by means of a screw cap, a rubber stopper or by connection of a stopcock, for example. The culture dishes are placed between a cover plate 4 and a base plate 5 and are pressed tightly in place by clamps 6. Resilient gaskets 7 are provided to stop any leakage between the uppermost dish and cover plate 4, and/or between dishes. Base plate 5 is provided to secure the bottom of the lowermost dish but is not necessary when the bottom of the lowermost dish is sufficiently rigid. Attached to the base plate 5 are adjustable feet 8 by which the cell attachment plate can be kept horizontally as shown in FIG. 2. Overflow passages 9 (FIG. 2) are provided through which the media, cell suspensions and gases can pass.

Figure 3:
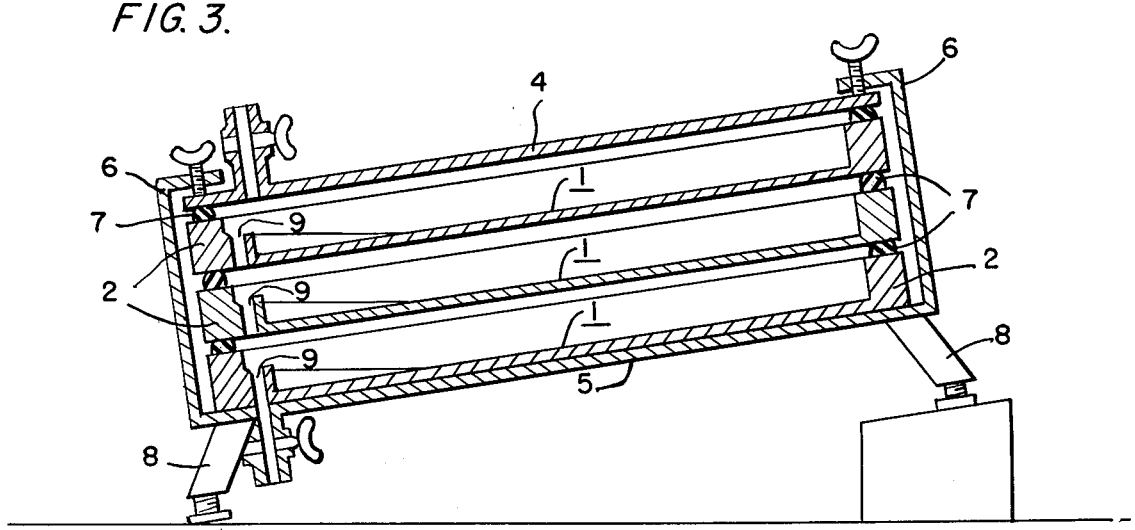
FIG. 3 is a side view, in cross-section, of the apparatus as shown in FIG. 2, illustrating diagrammatically one method of distributing the cell suspension in the culture medium.

In FIG. 3 of the drawings, a method is illustrated for dispensing a liquid, such as a cell suspension, evenly to all dishes. The quantity of media dispensed reaches its maximum when the cell attachment plate is horizontal and as the angle between the plate and the horizontal level inclines, the quantity of liquid involved in each dish decreases.

Figure 4:
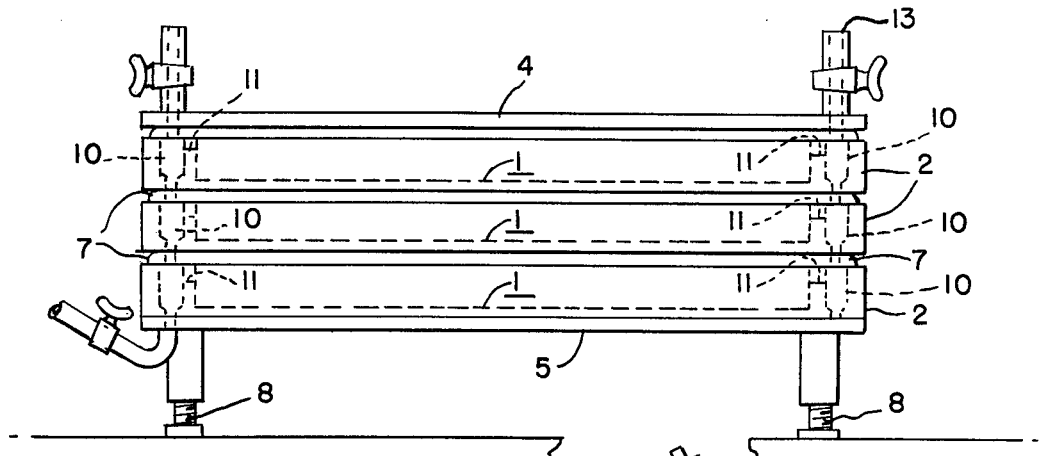
FIG. 4 is a side view, in cross-section, of the apparatus shown in FIG. 2, showing the dishes with two vertical holes having two lateral grooves connected thereto, through which liquid or gas can pass from one dish to another.
Figure 5:
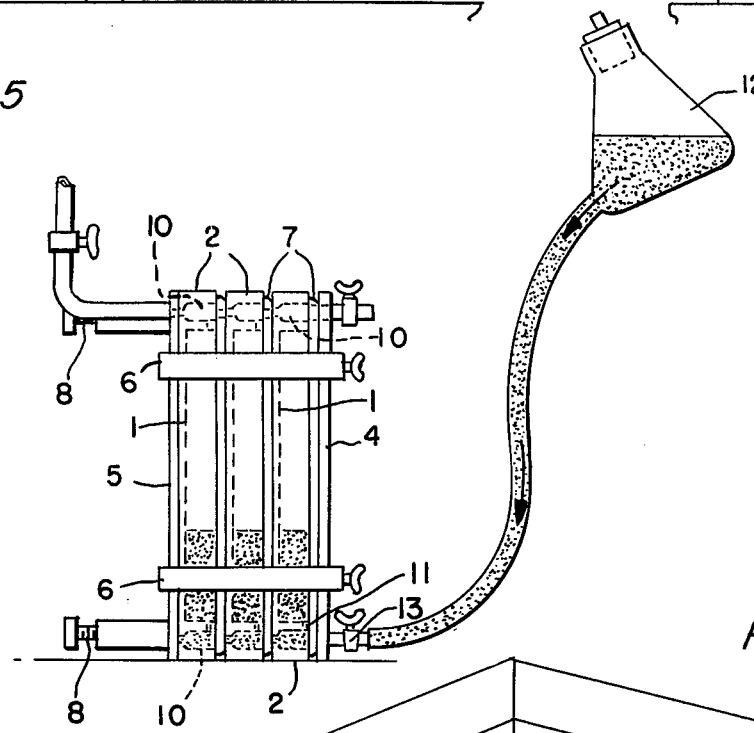
FIG. 5 is a diagrammatic representation showing the method for inoculating the cell suspension to the culture apparatus as shown in FIG. 4.

Referring now to FIGS. 4 and 5, inter-dish passages are provided by means of two vertical holes 10 connected with two lateral grooves 11 leading to the inside of each of the dishes through frames 2, through which the culture media and cells in reservoir 12 (FIG. 5) are poured from the inlet port 13 on cover plate 4 into all the dishes with even distribution. The height of reservoir 12 (FIG. 5) should be maintained above that of the culture apparatus to avoid flowback of the media into the reservoir.

Thus, by employing the aforementioned form of apparatus and method, a series of operations such as inoculation of cells, discarding of old media and replenishment of new media can be carried out simply and aseptically in a single action in the multimonolayer culture vessels. In addition, aseptically-filtered gases can be introduced through the port 13 on the cover or base plate into all the dishes through vertical holes 10 and lateral grooves 11 while the apparatus is in a horizontal arrangement.

Although the frames and cell attachment plates employed in this invention do not have to be joined together, the frames must have two sealing devices on the upside and downside in order to maintain tightness. Therefore, disposable cell attachment plates can be used when frames and cell attachment plates are not joined.

Figure 6:
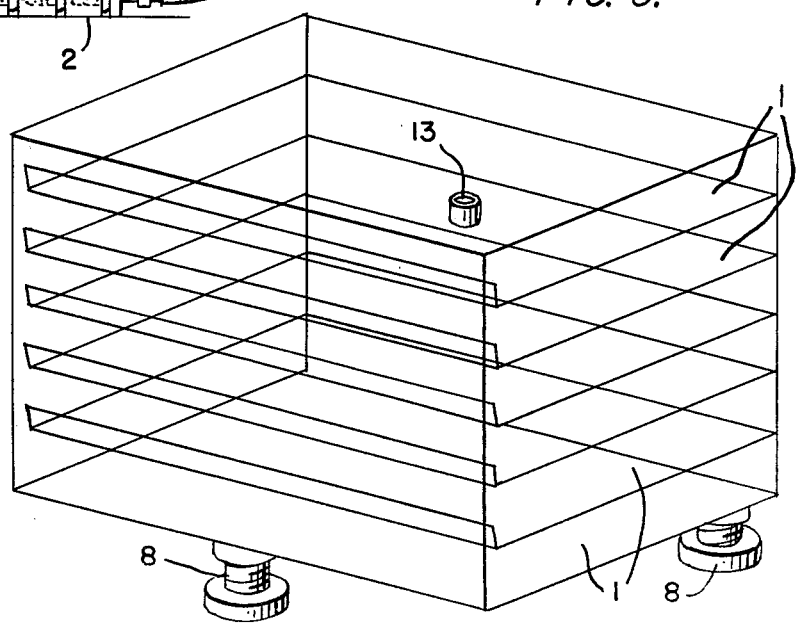
FIG. 6 is a view of another form of the apparatus of the present invention.
Figure 7:
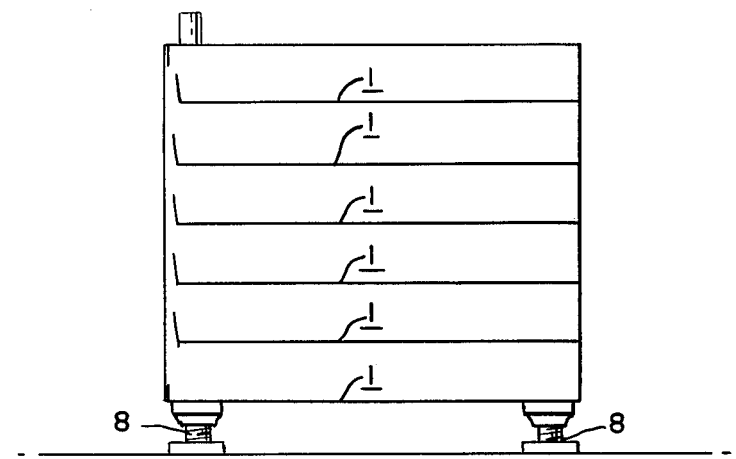
FIG. 7 is a side view of the container culture apparatus of FIG. 6.
Figure 7A:
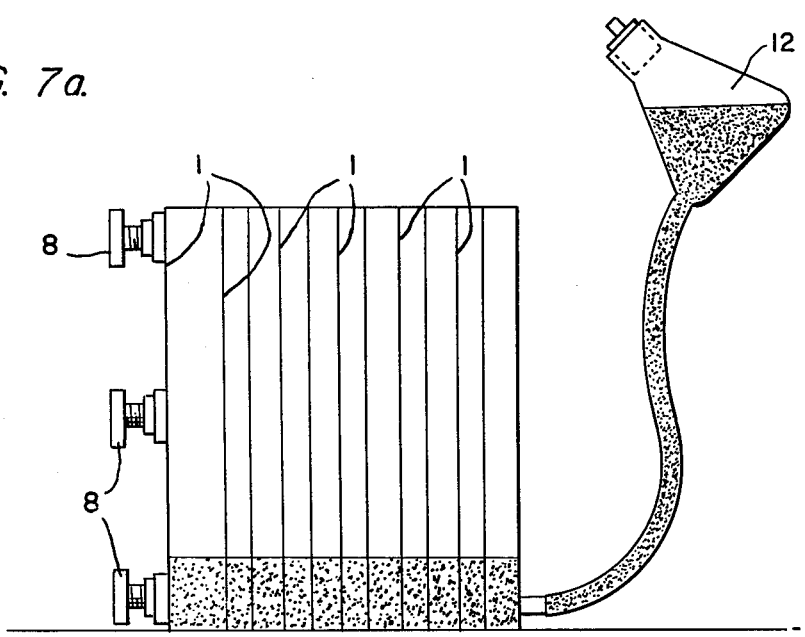
FIG. 7a is a side view of the apparatus of FIG. 7, with the lifted edges of the cell attachment plates standing in a vertical position.
Figure 7B:
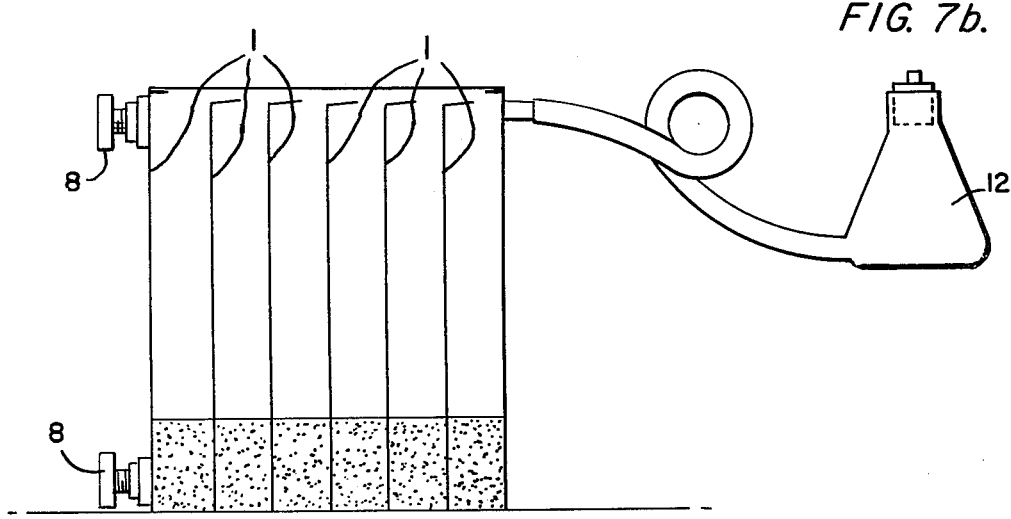
FIG. 7b is a side view of the apparatus of FIG. 7, with the lifted edges of the cell attachment plate sitting in a horizontal position.
Figure 7C:
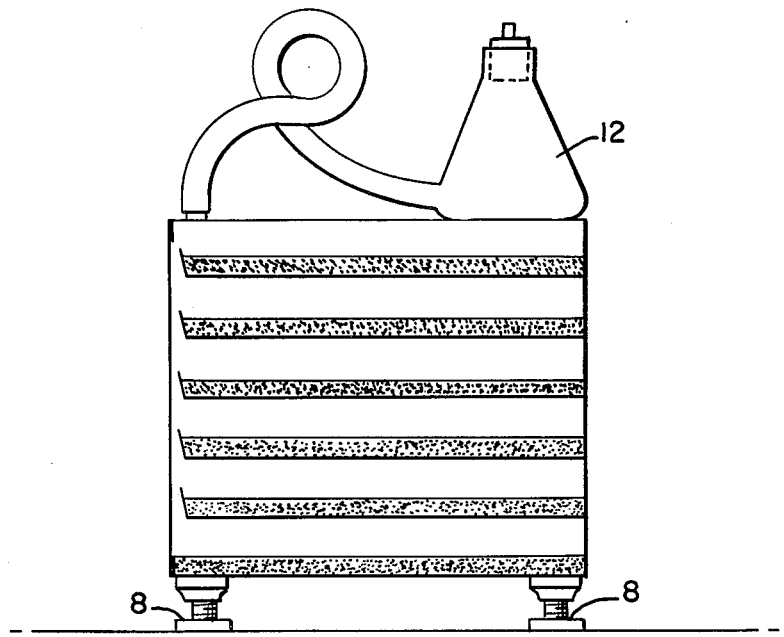
FIG. 7c is a side view of the apparatus of FIG. 7, with the apparatus in an upright position and the cell attachment plates having the cell suspension on them.

Referring now to FIGS. 6 and 7, in this form of the apparatus of the present invention, a portion of the edge of the cell attachment plates 1 fuses with the container side walls with the remaining portion of the edge of the cell attachment plates being turned up, thus holding the culture medium on the cell attachment plate. In this form of the apparatus of the present invention, the apparatus is turned laterally so that all turned up edges of the cell attachment plates stand in a vertical position as shown in FIG. 7a; the cell suspension is poured through the upper port and the apparatus is again turned laterally so that the turned up edges of the cell attachment plates lie in a horizontal position as shown in FIG. 7b. In this way, the cell suspension is equally dispensed into the sectionized spaces. Finally, the apparatus is again turned laterally bringing it to an upright position so that the cell suspension is maintained on the cell attachment plates as shown in FIG. 7c to permit formation of confluent monolayers of cells. Gases, such as a mixture of $CO_2$ and air, may be introduced through the inlet port to oxygenate the culture media and to adjust the pH of the culture media, with the container being tightly closed by means of the front panel which has a resilient gasket inside of it.

Figure 8:
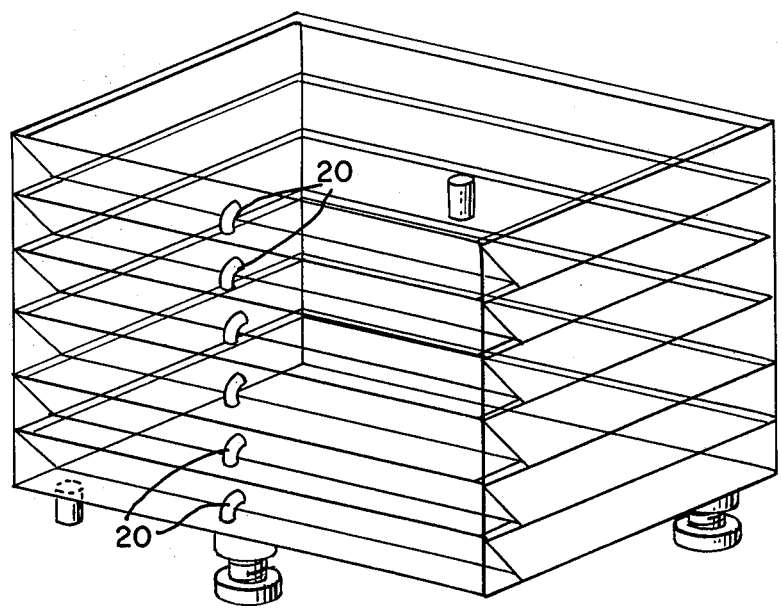
FIG. 8 is a view of the apparatus of FIG. 7, with overflow passages, and showing that the cell attachment plates can be removed.

Culture media and/or cell suspensions can be dispensed evenly through overflow passages 20, similar to those of FIG. 3, as illustrated in FIG. 8, and as shown in FIG. 8, these dishes with overflow passages can be removed from the container.

There is no limitation as to size or shape of the cell attachment plates utilized by the present invention, though substantial flatness is required. The surface material of the plate should be nontoxic for cell adherence and growth, and easily sterilizable, particularly by heating. Since microscopic observation or examination with the naked eye is desirable on occasion, the cell attachment plates should be transparent. Glass, polyethylene tenephthalate, polycarbonate or surface-activated methylpentene polymers are suitable substances for the cell attachment plate. If heat sterilization is not employed, polystyrene can also be used. In the use of methylpentene polymer which is transparent to ultraviolet light, sterilization can be carried out by external radiation with ultraviolet light (germicidal lamp).

Referring to the stacked-dish form of the present invention, the height of the frame enclosing the plate is the sum of the thickness of the liquid and gas phases and is generally about 4~50 m/m, but since a large surface area per total volume is generally required for large scale animal cell propagation, the height of the frame may be minimized to within the range of about 4 to 20 m/m. If the frames are composed of resilient material such as rubber, additional packings beyond the resilient gaskets provided (FIG. 1) are not necesary. The frames of this invention should be heat sterilizable and also non-toxic to the cells, and therefore may be made of stainless steel, aluminum, polycarbonate, methylpentene polymer, rubbers including silicon rubber, glass or other complexed material. If ethylene oxide gas is used as the sterilizing agent, most synthetic polymers can be employed in the culture apparatus. However, ethylene oxide gas is easily absorbed on the polymers and removal of the gas from the polymers is very time-consuming. The cover and base plates of the stacked-dish form of the present invention should also be transparent, heat sterilizable when possible, and non-toxic.

In the container form of the present invention, both the container and front panel are also preferably made of transparent, heat-sterilizable and non-toxic materials.

The following examples will further illustrate the apparatus and method of the present invention.

EXAMPLE 1

Human diploid strain WI-38 cells ($3 \times 10^7$) grown in five Roux bottles with a cell attachment area of 150 $cm^2$ per bottle were trypsinized with 0.25% trypsin and suspended in a nutrient medium comprising:

| Eagle's basal medium | 699 mls. |
|---|---|
| 7.5% Sodium bicarbonate | 13 mls. |
| 3.0% Glutamine | 8 mls. |
| Calf serum | 80 mls. |

The cell suspension was poured into the apparatus shown in FIG. 2 which comprised four plates (600 $cm^2$/plate) and was dispensed evenly over all the plates as illustrated in FIG. 3. The cells were grown at 37° C., on the plates (in a horizontal position) for 5 days with occasional gassing through a filter with a mixture of 3% $CO_2$ and 97% air for the purpose of attaining sufficient oxygen and for adjustment of the pH. The cell density attained was $5 \times 10^4/cm^2$. Microscopic examination showed no morphological differences between the cells grown in the apparatus of the present invention and those grown in the conventional Roux bottle.

EXAMPLE 2

A line of cells derived from rabbit kidney, $RK_{13}$ cells ($1.2 \times 10^8$) grown in conventional tissue culture bottles were digested with a mixture of 0.02% EDTA and 0.25% trypsin and suspended in a nutrient medium comprising:

| | |
|---|---|
| Eagle's basal medium | 1848 mls. |
| 7.5% Sodium bicarbonate | 32 mls. |
| 3.0% Glutamine | 20 mls. |
| Calf serum | 100 mls. |

The cell suspension was poured and dispensed into the apparatus of FIG. 6 comprising 10 dishes with a cell attachment area of 1000 cm$^2$/dish. The cell attachment plates were maintained in a horizontal position for 5 days with occasional aeration. Microscopic examination with a long-focus microscope showed that $RK_{13}$ cells formed a confluent monolayer on every cell attachment plate. The old culture medium was discarded and all the cell sheets were exposed to Newcastle disease virus (NDV) at an m.o.i. of 20 for inducing interferon. After absorption of the virus for one hour at 37° C., the non-absorbed NDV was removed by washing with serum-free medium. The cell sheets were replenished with 2 liters of fresh serum-free medium and further incubated at 37° C., for 24 hours, after which the culture fluid was collected, made clear by centrifuging, acidified to a pH of 2 to inactivate the NDV for four days, and neutralized. The neutralized preparation was analyzed for its viral interfering activity using vesicular stomatitis virus as the challenger virus. An interferon titer of 30,000 international units/ml. was obtained.

EXAMPLE 3

A strain of human diploid cells ($2 \times 10^7$ cells) derived from human fetal lung, cultivated in four Roux bottles of 150 cm$^2$/bottle was trypsinized and suspended in a nutrient medium comprising:

| | |
|---|---|
| Eagle's basal medium | 1750 mls. |
| 7.5% Sodium bicarbonate | 32 mls. |
| 3.0% glutamine | 20 mls. |
| Calf serum | 200 mls. |

The cell suspension was placed in the reservoir and poured into the apparatus as shown in FIG. 8, having overflow passages and comprising a polycarbonate container and ten glass dishes 20 cm × 30 cm in size. The apparatus was inclined to the degree necessary for 200 mls. of liquid to be contained on each dish, and then returned to the horizontal position. The cells attached to the submerged bottom of each dish and grew to form confluent monolayers on each dish after 5 days of cultivation at 37° C. The old medium was removed and the sheets were replenished with a new medium comprising:

| | |
|---|---|
| Eagle's basal medium | 1910 mls. |
| 7.5% Sodium bicarbonate | 32 mls. |
| 3.0% Glutamine | 20 mls. |
| Calf serum | 40 mls. |

After cultivation at 37° C. for one day, the medium was again removed. Five hundred milliliters of solution of a potent interferon inducer, polyriboinosinic polyribocytidylic acid complex Poly IC 10 μg./ml.) were added and dispensed evenly (50 mls. each) to all the cell sheets and remained in contact with the cell sheets for one hour at 37° C. After removal of non-absorbed poly IC, the front panel of the container was detached and each dish sequentially removed and irradiated with ultraviolet light (70,000 erg/cm$^2$) under aseptic conditions. The irradiated dishes were immediately returned to the container and the apparatus reconstructed. Serum-free medium (2 liters) was then fed onto the poly IC-stimulated and UV-irradiated cell sheets on each dish. Incubation was continued for an additional 24 hours at 37° C., after which time the supernatant fluid (about 2 liters) was harvested and found to contain 10,000 international units/ml. of human interferon.

Changes and modifications of the apparatus and method of this invention may be made within the scope of the appended claims.

What is claimed is:

1. A method of producing interferon, comprising the steps of: providing a plurality of substantially flat, substantially parallel plates adapted for the cultivation of tissue cells; sterilizing said plates; introducing a cell suspension onto said plates wherein said suspension comprises tissue cells and a culture medium; forming confluent monolayers of cells on said plates; oxygenating and adjusting the pH of said culture medium by exposure to a gas phase while maintaining said medium and said tissue cell monolayers in a static and undisturbed condition; exposing said tissue cell monolayers to interferon inducers and enhancers incubating said exposed tissue cell monolayers for formation of interferon therefrom; and collecting the crude interferon.

2. In a method of producing interferon, the steps comprising: providing an apparatus for propagating tissue culture cells comprising a plurality of spaced-apart, substantially flat plates on which cells, liquid and gas phases can exist, and means for maintaining said plates substantially parallel to each other, in which said plates are enclosed by frames to form dishes, wherein said dishes are easily separable from each other and are easily separable from the other components of the apparatus; sterilizing said apparatus; introducing a cell suspension to said plate, said suspension comprising tissue cells and a culture medium; forming substantially confluent monolayers of said cells on said plates; oxygenating and adjusting the pH of said medium by exposure to a gas phase while maintaining said medium and said tissue cell monolayers in a static and undisturbed condition; discarding the culture medium; stimulating said cells to produce interferon by exposure to interferon inducer and by irradiation of said cell monolayer with UV light; refeeding said cell monolayers with fresh serum-free medium; incubating said cell monolayers until sufficient interferon accumulates in the medium; and harvesting the crude interferon.

3. The method defined in claim 4 wherein the interferon inducer is a polyriboinosinic-polyribocytidylic acid complex.

4. The method defined in claim 4 comprising the further steps of:
removing each dish from said propagation apparatus for irradiation of said cell monolayers, and
replacing said dishes so as to reform said apparatus under aseptic conditions.

5. The method defined in claim 3 wherein said interferon inducers and enhancers are cycloheximide and actenomycin D.

* * * * *